(12) United States Patent
Lin et al.

(10) Patent No.: US 9,198,942 B1
(45) Date of Patent: Dec. 1, 2015

(54) **METHOD OF PREPARING BIOACTIVE COMPOUND FROM SOLID-STATE CULTIVATED *ANTRODIA CINNAMOMEA* MYCELIUM FOR ANTI-METASTASIS AGAINST LUNG CANCER CELLS**

(71) Applicant: TAIWAN LEADER BIOTECH CORP., Taipei (TW)

(72) Inventors: Chin-Chung Lin, Taipei (TW); Jong-Tar Kuo, Taipei (TW); Ching-Chun Chen, Taipei (TW); Jent-turn Lee, Taipei (TW); Yu-Yen Lin, Taipei (TW)

(73) Assignee: TAIWAN LEADER BIOTECH CORP., Taipei (TW)

( * ) Notice: Subject to any disclaimer, the term of this patent is extended or adjusted under 35 U.S.C. 154(b) by 0 days.

(21) Appl. No.: 14/461,552

(22) Filed: Aug. 18, 2014

(51) Int. Cl.
| | |
|---|---|
| *C07C 41/36* | (2006.01) |
| *C07C 41/34* | (2006.01) |
| *A61K 36/07* | (2006.01) |
| *A61K 31/09* | (2006.01) |

(52) U.S. Cl.
CPC ............... *A61K 36/07* (2013.01); *A61K 31/09* (2013.01); *C07C 41/34* (2013.01); *C07C 41/36* (2013.01)

(58) Field of Classification Search
None
See application file for complete search history.

(56) References Cited

U.S. PATENT DOCUMENTS

| | | | |
|---|---|---|---|
| 2010/0286227 A1* | 11/2010 | Sheu et al. | 514/423 |
| 2012/0029069 A1* | 2/2012 | Lee et al. | 514/464 |

OTHER PUBLICATIONS

Database CAPLUS in STN, Acc. No. 1993:603146, Shinkawa et al., JP 05148176 A (Jun. 15, 1993) (abstract).*
Chen et al., Phytomedicine (2012), 19(8-9), pp. 768-778.*
Hsu et al., Food and Chemical Toxicology (2007), 45(7), pp. 1249-1257.*
Kumar et al., Journal of Ethnopharmacology (2011), 136(1), pp. 168-177.*

* cited by examiner

*Primary Examiner* — Brian J Davis
(74) *Attorney, Agent, or Firm* — Jackson IPG PLLC; Demian K. Jackson

(57) ABSTRACT

A bioactive compound obtained from *A. cinnamomea* mycelium is prepared. The *A. cinnamomea* mycelium is solid-state cultivated. The bioactive compound is 2,3,6-trimethoxy-4-methylphenol and is called Leader 1. Leader 1 effectively suppresses movement, migration and invasion of lung cancer cells. Leader 1 achieves the effect of anti-metastasis and shows excellent resistance to physiological activity and mechanism on cancer metastasis.

4 Claims, 11 Drawing Sheets

METHOD OF PREPARING BIOACTIVE COMPOUND FROM SOLID-STATE CULTIVATED *ANTRODIA CINNAMOMEA* MYCELIUM FOR ANTI-METASTASIS AGAINST LUNG CANCER CELLS

FIELD OF THE INVENTION

The present invention relates to extract *Antrodia cinnamomea* mycelium; more particularly, relates to prepare a bioactive compound from solid-state cultivated *A. cinnamomea* mycelium for anti-metastasis against lung cancer cells.

BACKGROUND OF THE INVENTION

Carcinogenesis happens according to several factors, such as age, diet, lifestyle, and genetic and environmental causes. Cancer is one of the leading diseases of death, and the causes of death of cancer patients are often due to metastasis of tumor cells. Hence, how to effectively control the tumor cells and suppress their metastases becomes a very important strategy for cancer therapy.

The processes of cancer cells metastasis include adhesion, invasion and migration. The cancer metastasis requires matrix metalloproteinases (MMP) to break down extracellular matrixes (ECM) and process epithelial-mesenchymal transitions (EMT). Meanwhile, related proteins for cancer cells metastasis will greatly express to promote the occurrence of cancer metastasis.

Tumor necrosis factor (TNF) is a small-molecule protein (cytokine) secreted by macrophage. Therein, tumor necrosis factor-α (TNF-α) is mainly secreted by monocyte-macrophage. Many previous studies indicate TNF-α promotes invasion and metastasis of cancer cells.

*A. cinnamomea* is a precious medicinal fungus indigenous to Taiwan. According to the previously studied, it has been proven that the methanol- and hot water-extracts of *A. cinnamomea* possessed excellent anti-inflammatory activity. Besides, many studies pointed out that the mycelium and fruiting body of *A. cinnamomea* presented the potent anticancer activity. However, the mechanism and activity of *A. cinnamomea* extracts and/or benzoic compounds, which involved in cancer metastasis, are still unclear.

Hence, the prior arts do not fulfill all users' requests on actual use.

SUMMARY OF THE INVENTION

The main purpose of the present invention is to prepare a bioactive compound (Leader 1) from solid-state cultivated *A. cinnamomea* mycelium for suppressing metastasis of lung-cancer cells.

To achieve the above purpose, the present invention is a method of preparing an extracts from solid-state cultivated *A. cinnamomea* mycelium for anti-metastasis against lung-cancer cells, comprising steps of (a1) providing a dried solid-state cultivated *A. cinnamomea* mycelium; and (b1) extracting the dried solid-state cultivated *A. cinnamomea* mycelium at a room temperature by using an ethanol to obtain an extract.

Or, the present invention can comprise steps of (a2) providing a dried solid-state cultivated *A. cinnamomea* mycelium; (b2) extracting *A. cinnamomea* mycelium at the room temperature by using an ethanol to obtain an extract; (c2) condensing the ethanolic extracts to obtain a condensed product; and (d2) partitioning the condensed product by using ethyl acetate and water to obtain an ethyl acetate soluble extracts.

Accordingly, a novel method of preparing a bioactive compound (Leader 1) of solid-state cultivated *A. cinnamomea* mycelium for anti-metastasis to lung cancer cells is obtained.

BRIEF DESCRIPTION OF THE DRAWINGS

The present invention will be better understood from the following detailed description of the preferred embodiment according to the present invention, taken in conjunction with the accompanying drawing(s), in which.

DESCRIPTION OF THE PREFERRED EMBODIMENT

Figure 1:
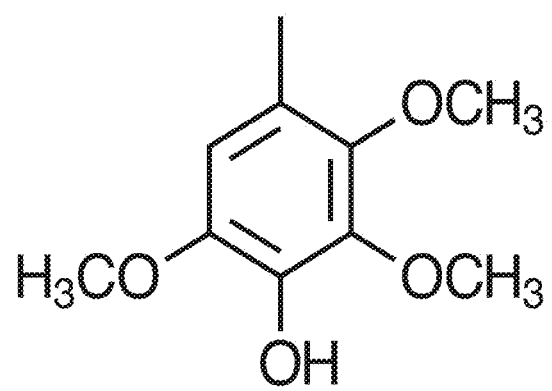
FIG. 1 is the structural view showing the bioactive compound (Leader 1) prepared through the preferred embodiment according to the present invention.

The following description of the preferred embodiment is provided to understand the features and the structures of the present invention.

Please refer to FIG. 1 to FIG. 8B, which are a view showing a bioactive compound (Leader 1) prepared through a preferred embodiment according to the present invention; views showing cell survival rate, wound healing ability and cell migration ability affected by Leader 1; and views showing expressions of matrix metalloproteinases (MMP-2, MMP-9); an original plasminogen activator in lung cancer cells; and related proteases and proteins, affected by Leader 1. As shown in the figures, the present invention is a method of preparing a bioactive compound from solid-state cultivated *A. cinnamomea* mycelium for anti-metastasis to lung-cancer cells. The bioactive compound, which chemical formula is 2,3,6-trimethoxy-4-methylphenol and is also called 'Leader 1', shows an excellent performance on suppressing cancer metastasis.

The present invention uses TNF-α to induce A549 lung cancer cells for acquiring the role of Leader 1 on participating in suppressing lung cancer metastasis.

State-of-Use 1: Preparation

[Material]

The present invention uses *A. cinnamomea* mycelium, which is solid-state cultivated through a technology developed by Taiwan Leader Biotech Corp. The present invention also purchases fetal bovine serum (FBS) from Gibco BRL (Invitrogen, Grand Island, N.Y.); and purchases penicillin; dimethyl sulfoxide (DMSO); 3-(4,5-dimethylthiazol-2-yl)-2, 5-diphenyl tetrazolium bromide (MTT); Gimsa; and casein, from Sigma-Aldrich (St Louis, Mo.). All chemicals and solvents used in the present invention are agents or products of high-performance liquid chromatography (HPLC) grade.

[Cell Culture]

The present invention selects a human lung cancer cell, A549, for exploring lung cancer cell metastasis. For culturing A549, the A549 cells grown in 75 T flask are replanted in a 10 square-centimeter (cm²) dish at a seeding density of 2×10⁵ cells per square-centimeter (cells/cm²) to be cultured at 37 Celsius degrees (° C.) in an incubator having 5% carbon dioxide (CO₂). The culture medium used is Ham's F12 (which is recommended by Bioresources Collection and Research Center (BCRC), Taiwan, and American Type Culture Center (ATCC)) and is added with extra 10% fetal bovine serum.

State-of-Use 2: Preparing Extracts of Solid-State Cultivated *Antrodia cinnamomea* Mycelium At first, the solid-state cultivated *A. cinnamomea* mycelium is dried by a cold-air dryer. Then, 2000 g of the dried *A. cinnamomea* mycelium is extracted at 25° C. with a 95% ethanol water solution (V/V) for obtaining an ethanol extract (ACME).

Then, the ethanol extract is concentrated in vacuum to obtain 323.6 g of a concentrated product. Then the concentrated product is partitioned into an EA-separated part and a water-soluble part with 100% v/v of ethyl acetate (EA) and water. Therein, the water-soluble part is labeled as ACME-water; and, the EA-separated part is labeled as ACME-EA, which contains the final extracted material prepared according to the present invention.

State-of-Use 3: Isolation and Purification of Leader 1

The ACME-EA obtained in state-of-use 2 is divided into nine separated sub-fractions of concentration gradient in mobile phase by using column chromatography. Therein, the column chromatography uses a silica gel (230~400 mesh) for a stationary phase and a mixed solution of n-hexane/ethyl acetate for a mobile phase; and, the concentration gradient is obtained in the mobile phase of the column chromatography with the mixed solution of n-hexane/ethyl acetate at concentration ratios of 100:0, 90:10 80:20, 70:30, 60:40, 50:50, 30:70, and 0:100.

Then, the fourth divided sub-fraction is purified by high performance liquid chromatography (HPLC), where the mobile phase is n-hexane/ethyl acetate mixed solution (volume ratio of 77:23); the flow rate is 5 ml/min; the detector is an ultraviolet (UV) detector with wavelength of 254 nm. The structure of bioactive compound is identified by mass spectrum analysis to obtain its molecular weight as 198.09 and its chemical formula figured out as $C_{10}H_{14}O_4$. The structural formula is further confirmed by $^1H$ and $^{13}C$ nuclear magnetic resonances (NMR) as follows:

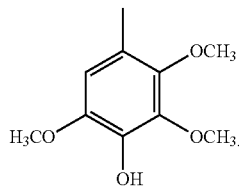

In, FIG. 1, the bioactive compound is identified as 2,3,6-trimethoxy-4-methylphenol (Leader 1).

State-of-Use 4: Using Leader 1 for Obtaining Ability on Suppressing Survival Rate of A549

At first, A549 cells are cultured as described in state-of-use 1. After being washed with tripsin, the cells are replanted for 24 hr in a dish having 24 wells at a seeding density of 2×10⁵ cells/cm². In Table 1, Leader 1 having a concentration of 0, 5, 10, or 40 μM is cultured for 24 hr to be applied to A549, where Leader 1 having 0 μM is added with DMSO to be used as a control group. Then, Leader 1 is removed and 5 mg/ml of MTT is added for reaction for 2 hr, where MTT is a water-soluble tetrazolium salt and is appeared to be pale yellow after being dissolved in phosphate buffered saline (PBS). Through a reduction of dehydrogenase in mitochondria, the cyclic structure of MTTs becomes water-insoluble blue-violet crystals. Then, the cell membrane and the blue-violet crystals are dissolved with DMSO to acquire light-absorbance rates with a wavelength of 570 nm for forming a statistical diagram by using sigma plot 10.0.

TABLE I

| Groups | Control group | 5 | 10 | 20 | 40 |
|--------|---------------|-----|------|------|------|
| Dosing | DMSO 0.05% | 5 μM | 10 μM | 20 μM | 40 μM |

Figure 2:
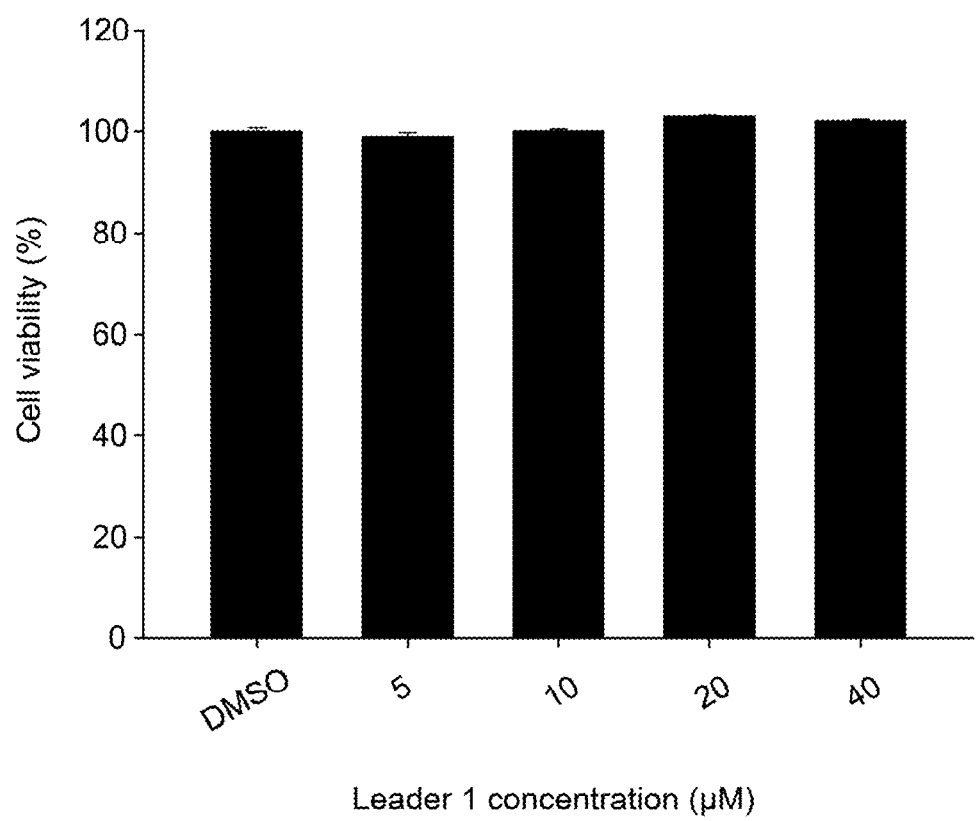
FIG. 2 is the view showing the cell survival rate affected by Leader 1.

In FIG. 2, Leader 1 does not affect survival rate of lung cancer cells, where there is no difference in survival rate for the concentrations of 0~40 μM and, thus, no cytotoxicity to lung cancer cells is shown.

State-of-Use 5: Using Leader 1 for Obtaining Ability on Suppressing Wound Healing of A549

At first, lung cancer cells A549 are cultured as described in state-of-use 1. After being washed down with tripsin, the cells are replanted in a 12-well plate at a seeding density of 2×10⁷ cells/cm² for 24 hr for attachment. Then, a wound line is made in each well. After floating part of the cells are removed by being slight-washed with PBS, the cells are added to culture media having concentrations of 0, 5, 10, 20 and 40 μM of Leader 1 for observation at time points of 0, 12, 24 or 48 hr to be photographed as records, where a medium dosed with 0 μM of DMSO is used as a control group.

Figure 3:
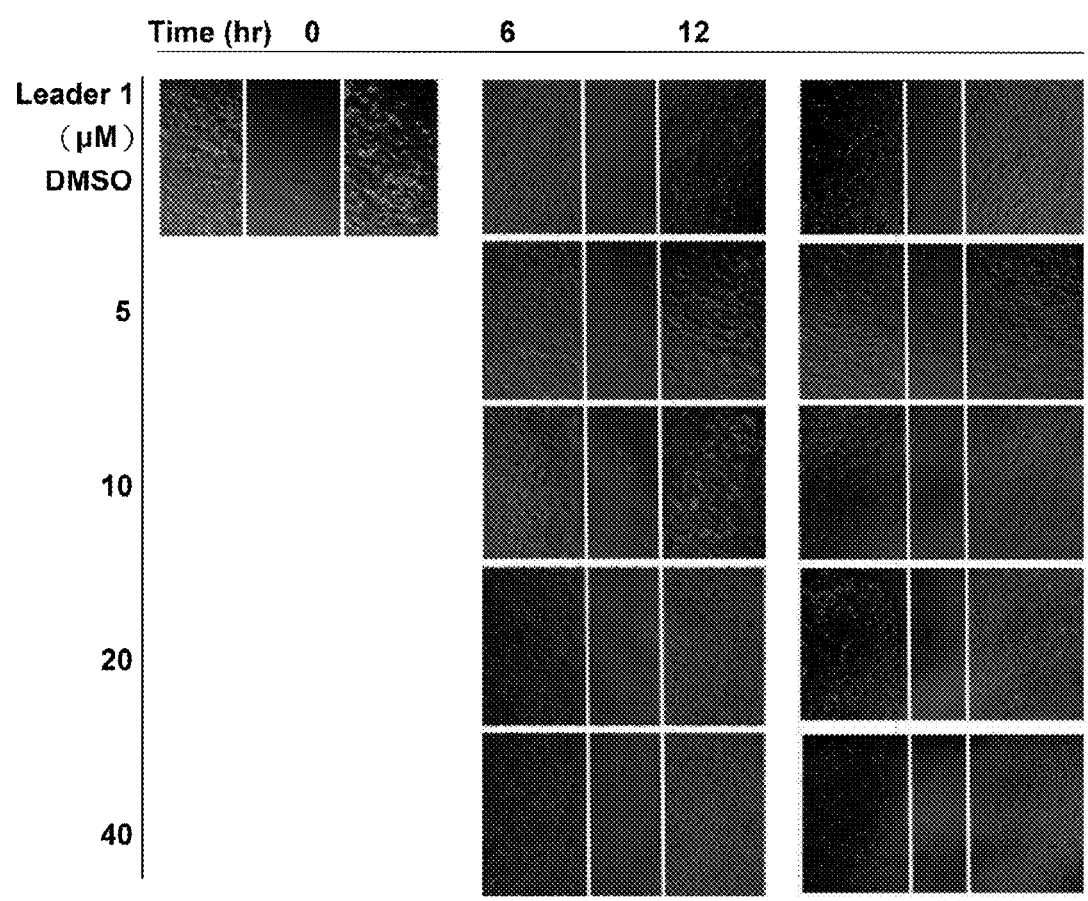
FIG. 3 is the view showing the wound healing ability affected by Leader 1.

In FIG. 3, Leader 1 shows its ability on suppressing wound healing of lung cancer cells, especially that having a concentration of 40 μM.

State-of-Use 6: Using Leader 1 for Obtaining Ability on Suppressing Migration of A549 Cells 24-well transwell kits (Millipore Co.) are used for analyzing lung cancer cell migration.

At first, lung cancer cells A549 are cultured as described in state-of-use 1. After being washed down with tripsin, the cells are replanted in a 12-well plate at a seeding density of 2×10⁵ cells/cm² for 24 hr for attachment. After being added into media having concentrations of 0, 5, 10 and 40 μM of Leader 1 for 24 hr, the cells are rinsed with PBS and, then, dropped down with tripsin. The cells are loaded into centrifuge tubes for centrifugal rotation at a speed of 1280 rpm for 3 min to remove supernatant. Residual serum is removed by slow-washing with PBS. Then, centrifugal rotations are processed at a speed of 1280 rpm for 3 min. The cells are added into culture media at a density of 2×10⁵ cells/cm², where the media are located at an upper layer of the kit and injected with a 200 μl solution containing only 0.1% fetal bovine serum. Another media are located at a lower layer of the kit and containing 20% fetal bovine serum (induced or not induced with TNF-α). The kit having the two layers of media is put in an incubator to be observed after 12 or 24 hr.

The kit is taken out to be slowly wetted with double distilled water (ddH₂O); and, part of the cells which do not penetrate through wells are removed by a cotton swab. The kit is soaked in methanol and stayed still for 20 min to be dried afterwards. Then, the kit is soaked in Gimsa to be dyed for 20 min. After being soaked in ddH₂O for a few minutes, the kit is dried for observing migration of the cells with a microscope; and, the dyed cells are photographed by digital camera for statistical mapping with sigma plot 10.0.

Figure 4A:
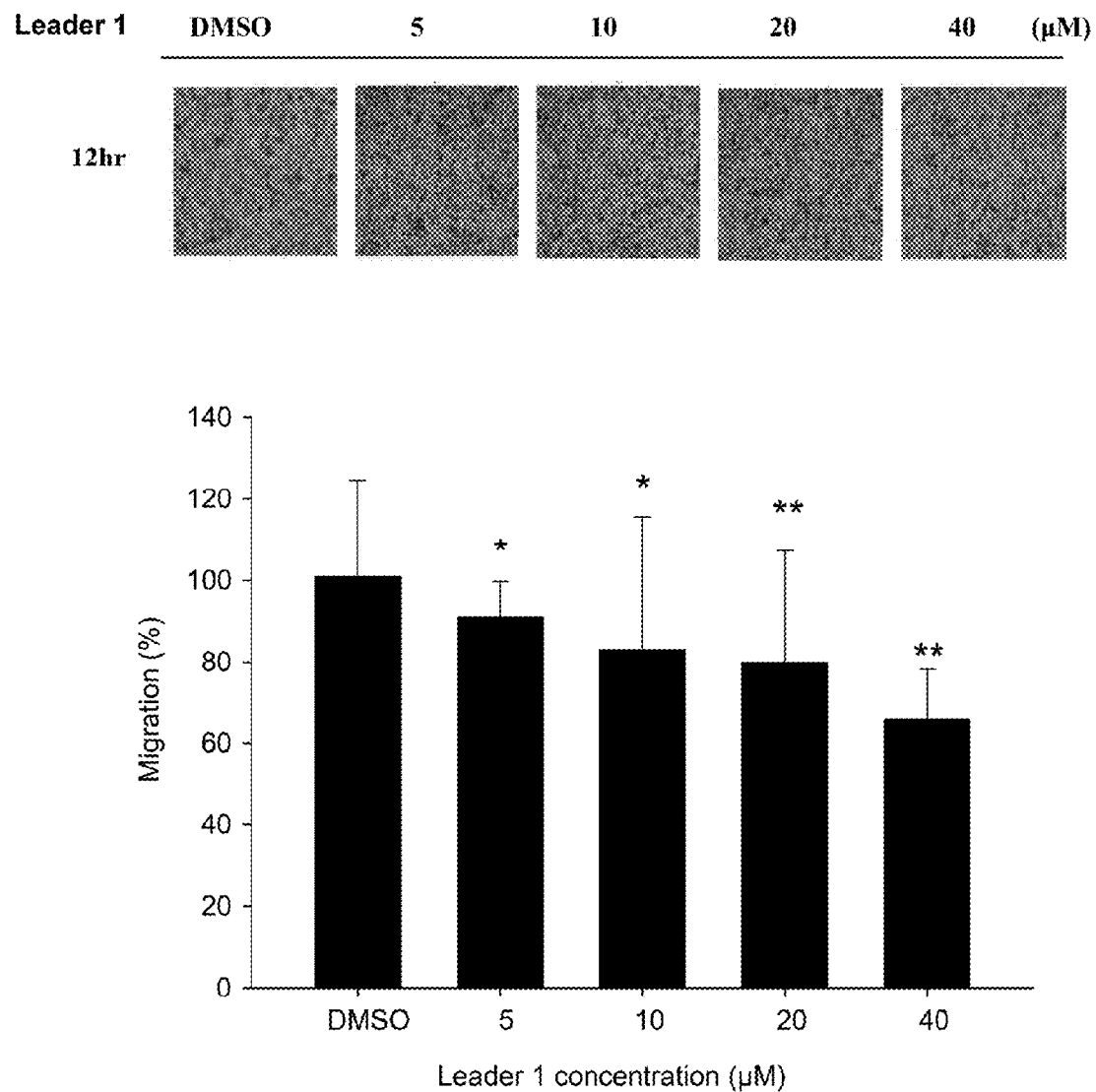
FIG. 4A and FIG. 4B are the views showing the cell migration ability affected by Leader 1.
Figure 4B:
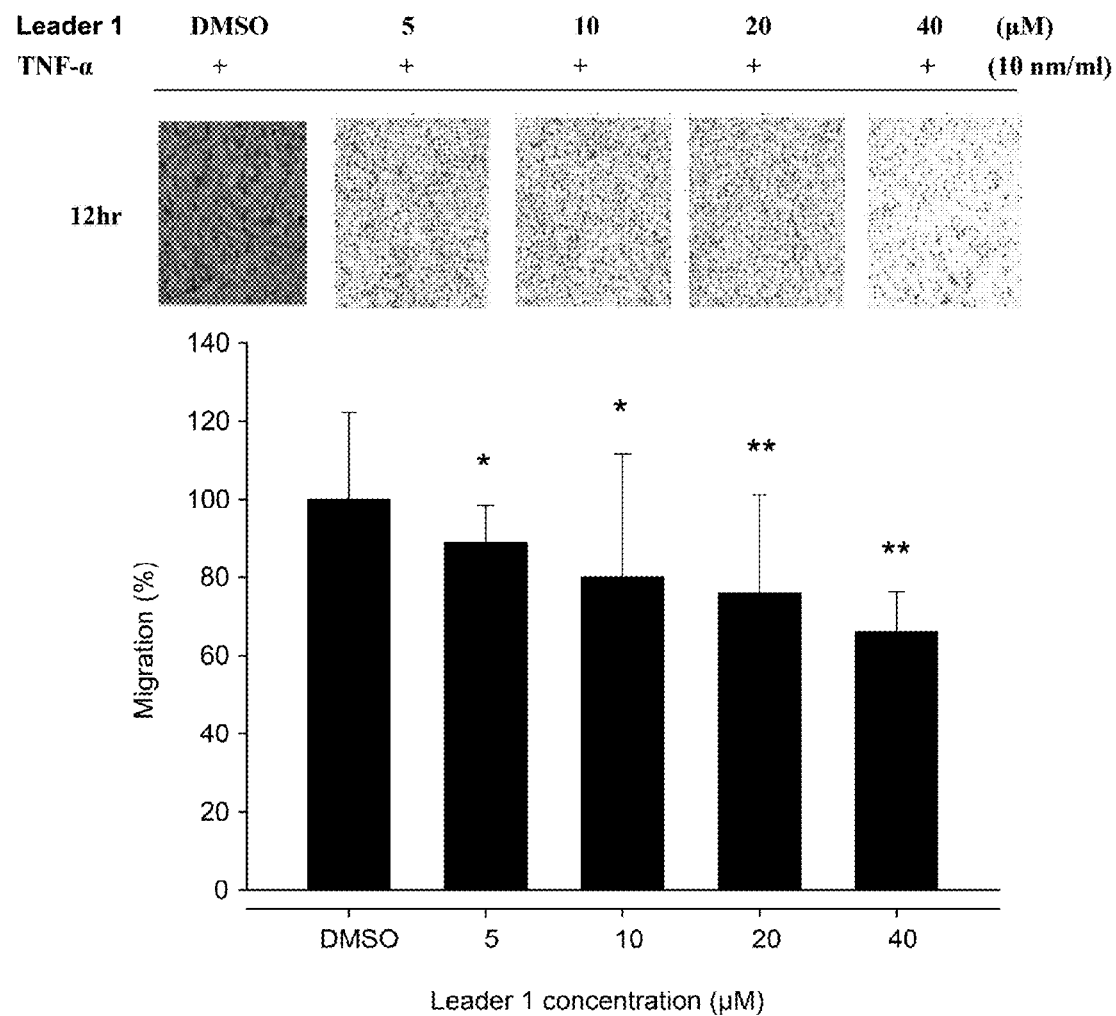

In FIG. 4A and FIG. 4B, Leader 1 shows activity on suppressing migration of lung cancer cells, especially Leader 1 having the dosage of 40 µM.

State-of-Use 7: Using Leader 1 for Obtaining Ability on Suppressing Invasion of A549 Cells The 24-well kit is used for analyzing lung cancer cell invasion. The kit is prepared by injecting Matrigel (3 mg/ml-well, BD science) into the upper layer of the kit, to be placed in an incubator for 24 hr and, then, process solidification.

At first, lung cancer cells A549 are cultured as described in state-of-use 1. After being washed down with tripsin, the cells are replanted in a 6-well plate at a seeding density of $2\times10^5$ cells/cm$^2$ for 24 hr for attachment. After being added into media having concentrations of 0, 5, 10 and 40 µM of Leader 1 for 24 hr, the cells are rinsed with PBS and, then, dropped down with tripsin. The cells are loaded into centrifuge tubes for centrifugal rotation at a speed of 1280 rpm for 3 min to remove supernatant. Residual serum is slowly removed by washing with PBS. Then, centrifugal rotations are processed at a speed of 1280 rpm for 3 min. The cells are added at a density of $2\times10^5$ cells/cm$^2$ into culture media, where the media are located at the upper layer and injected with a 200 µl solution containing only 0.1% fetal bovine serum. Another media are located at the lower layer and contain 20% fetal bovine serum. The kit is put in an incubator to be observed after 12 or 24 hr.

The kit is taken out to be slowly wetted with ddH$_2$O; and, a cotton swab removes part of the cells, which do not penetrate through wells. The kit is soaked in methanol and stayed still for 20 min to be dried afterwards. Then, the kit is soaked in Gimsa to be dyed for 20 min. After being soaked in ddH$_2$O for a few minutes, the kit is dried for observing migration of the cells with a microscope; and, the dyed cells are photographed by camera for statistical mapping with sigma plot 10.0.

Figure 5:
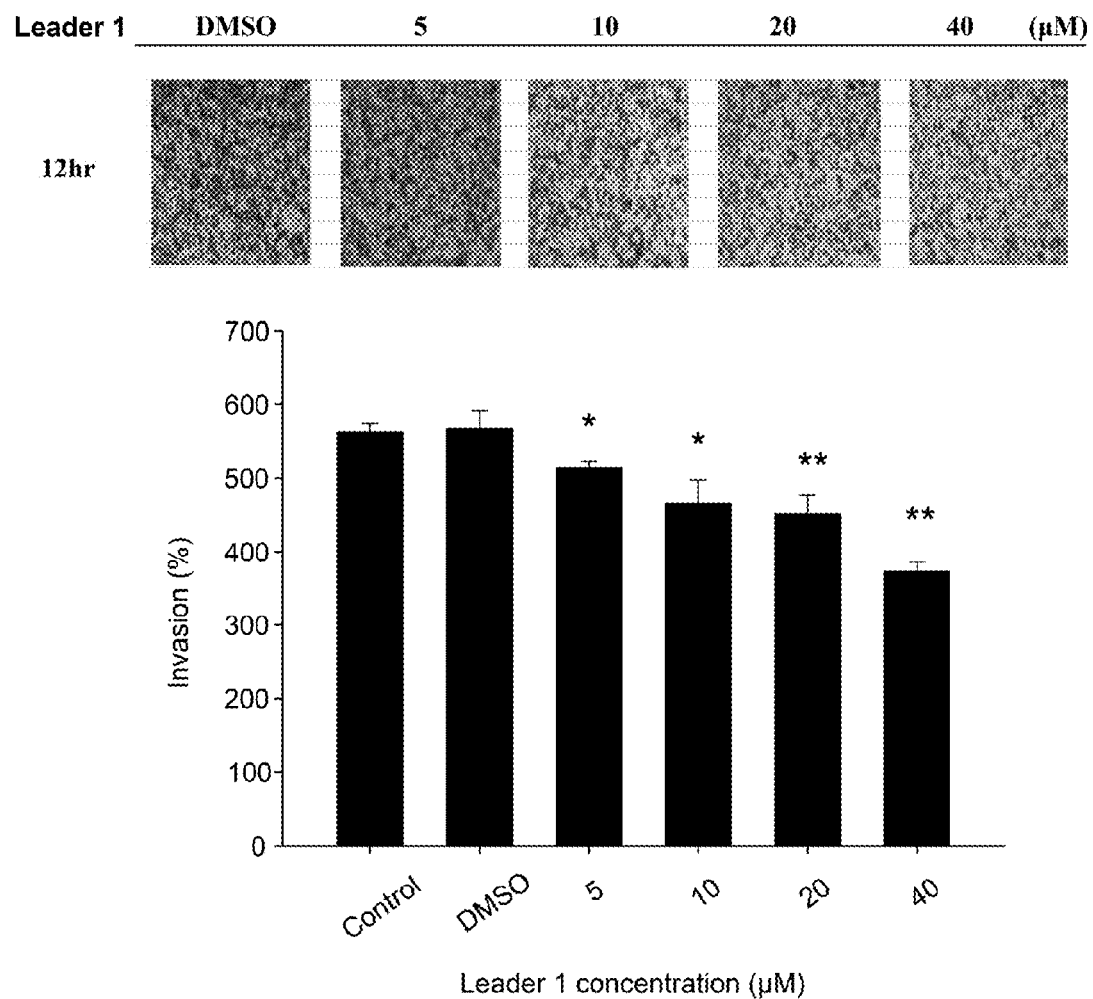
FIG. 5 is the view showing the invasion ability affected by Leader 1.

In FIG. 5, Leader 1 shows ability on suppressing invasion of lung cancer cells, especially Leader 1 having the dosage of 40 µM.

State-of-Use 8: Using Leader 1 for Obtaining Ability on Suppressing Matrix Metalloproteinase of A549 Cells Electrophoresis is used to detect hydrolytic enzymes. Gelatin zymography is used to analyze activities of gelatinases (MMP-2, MMP-9) in matrix metalloproteinase (MMP) of lung cancer cells.

At first, lung cancer cells A549 are cultured as described in state-of-use 1. After being washed down with tripsin, the cells are replanted in a 12-well plate at a seeding density of $2\times10^5$ cells/cm$^2$ for 24 hr for attachment. Then, the kit is rinsed with PBS two times. After being added into media having concentrations of 0, 5, 10 and 40 µM of Leader 1 for 24 hr, the cells are added into media having 1% fetal bovine serum for 24 hr for obtaining culture media containing the cells. The kit is put into an Eppendorf centrifuge tube for centrifugal rotation at a 1250 rpm speed for 10 min. Then, the supernatant is taken out to be stored at –20° C.

An equivalent amount of the supernatant is added into 8%-gradient colloidal wells of gel (SDS-PAGE, containing 1 mg/ml gelatin) with a 6-times MMP dye. A running buffer is added and reaction stops after 45 kD of a MMP marker is resolved into the gel with a current of 80 V and 300 mA.

The gel is taken out for reaction in a zymography renaturing buffer at a 35 rpm speed. The reaction is done for 2 times at a room temperature and it takes 30 min for each time. After SDS contained in the gel is removed, the zymography developing buffer is used for reaction for 20~24 hr at a 35 rpm speed under 37° C. and then is removed. Coomassie blue R-250 is used for dyeing for 30 min. ddH$_2$O is used for soaking overnight. Then, the gel is put into a digital image analyzer (Chemi-smart 3000) for photographic analysis for statistical mapping with sigma plot 10.0.

Figure 6A:
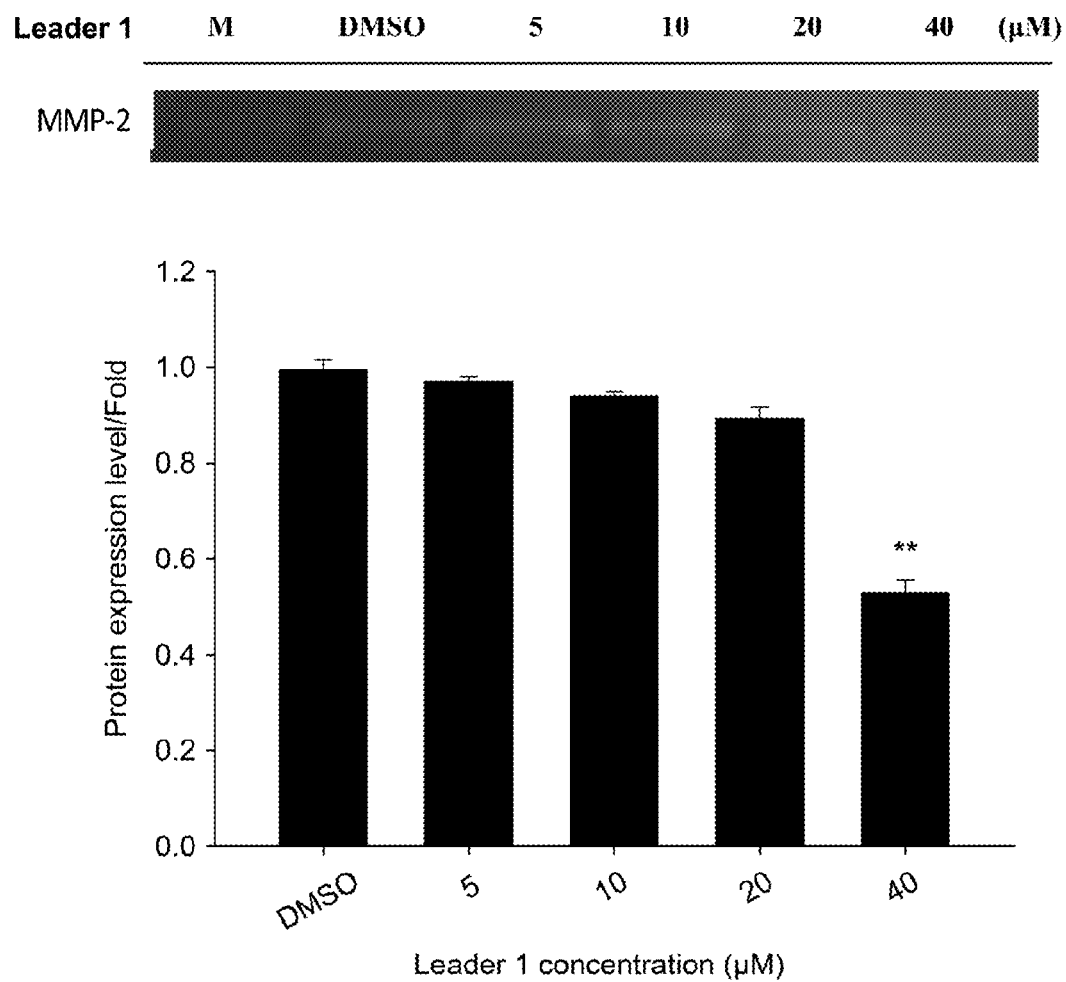
FIG. 6A and FIG. 6B are the views showing the expressions of the matrix metalloproteinases (MMP-2, MMP-9)
Figure 6B:
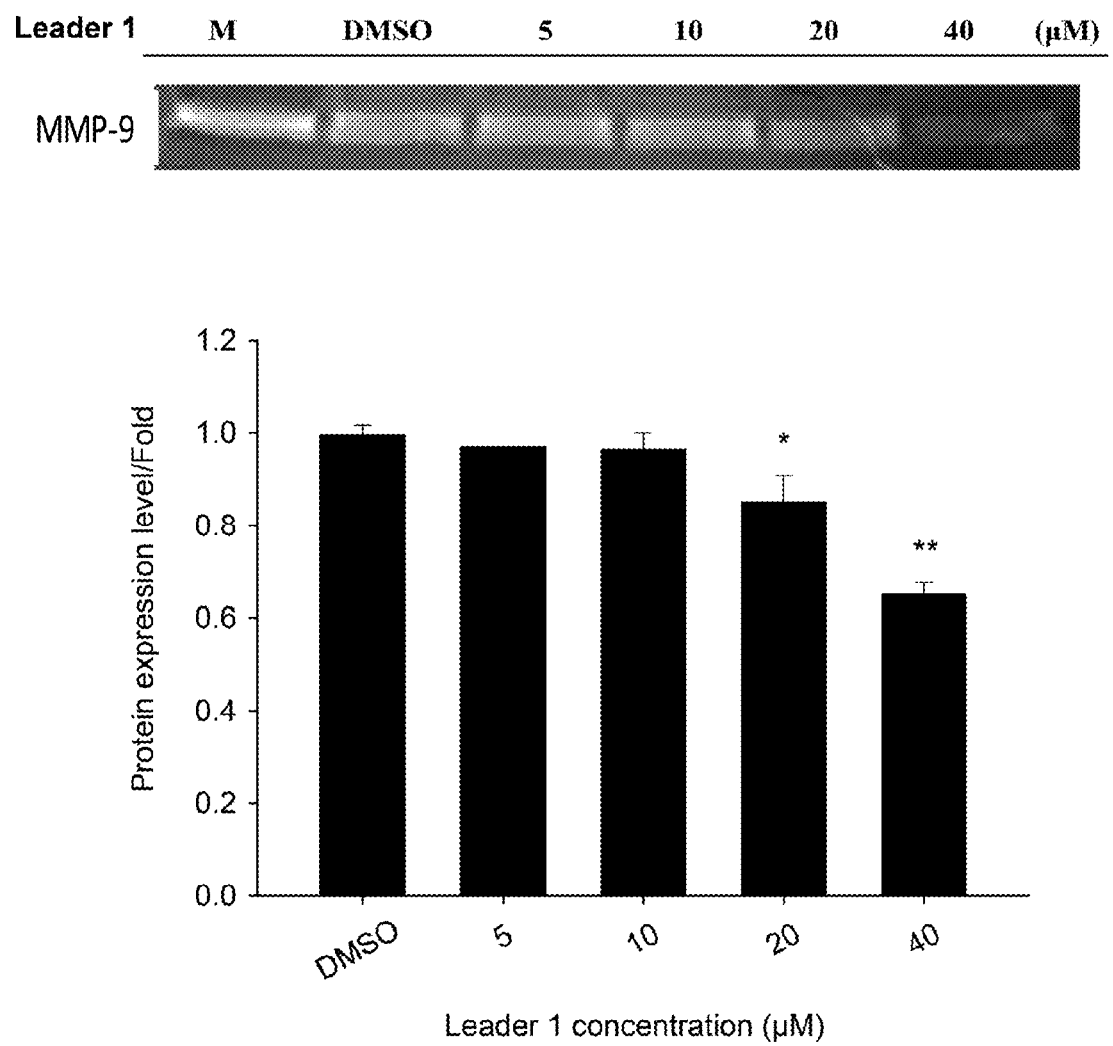

In FIG. 6A and FIG. 6B, Leader 1 shows ability on suppressing matrix metalloproteinase (MMP-2, MMP-9) activity of lung cancer cells, especially Leader 1 having the dosage of 40 µM.

State-of-Use 9: Using Leader 1 for Obtaining Ability on Suppressing Plasminogen Activator of A549 Cells Electrophoresis is used for detecting hydrolytic enzymes. The part regarding plasminogen in casein-zymography is used for analyzing activity of urokinase-type plasminogen activator (uPA) of lung cancer cells, where uPA would decompose plasminogen into plasmin.

At first, lung cancer cells A549 are cultured as described in state-of-use 1. After being washed down with tripsin, the cells are replanted in a 12-well plate at a seeding density of $2\times10^5$ cells/cm$^2$ for 24 hr for attachment. Then, the kit is rinsed with PBS two times. After being added into media having concentrations of 0, 5, 10 and 40 µM of Leader 1 for 24 hr, the cells are added into media having 1% fetal bovine serum for 24 hr for obtaining culture media containing the cells. The kit is put into an Eppendorf centrifuge tube for centrifugal rotation at a 1250 rpm speed for 10 min. Then, the supernatant is taken out to be stored at –20° C.

An equivalent amount of the supernatant is added into 8%-gradient colloidal wells of gel (containing 15 µl/ml plasminogen and 1 mg/ml gelatin) with a 6-times MMP dye. A running buffer is added and reaction stops after 45 kD of a MMP marker is resolved into the gel with a current of 80 V and 300 mA.

The gel is taken out for reaction in a zymography renaturing buffer at a 35 rpm speed. The reaction is done for 2 times at a room temperature and it takes 30 min for each time. After SDS contained in the gel is removed, the zymography developing buffer is reacted for 20~24 hr at a 35 rpm speed under 37° C. and then is removed. Coomassie blue is used for dyeing for 30 min. ddH$_2$O is used for soaking overnight. Then, the gel is put into a digital image analyzer for photographic analysis for statistical mapping with sigma plot 10.0.

Figure 7:
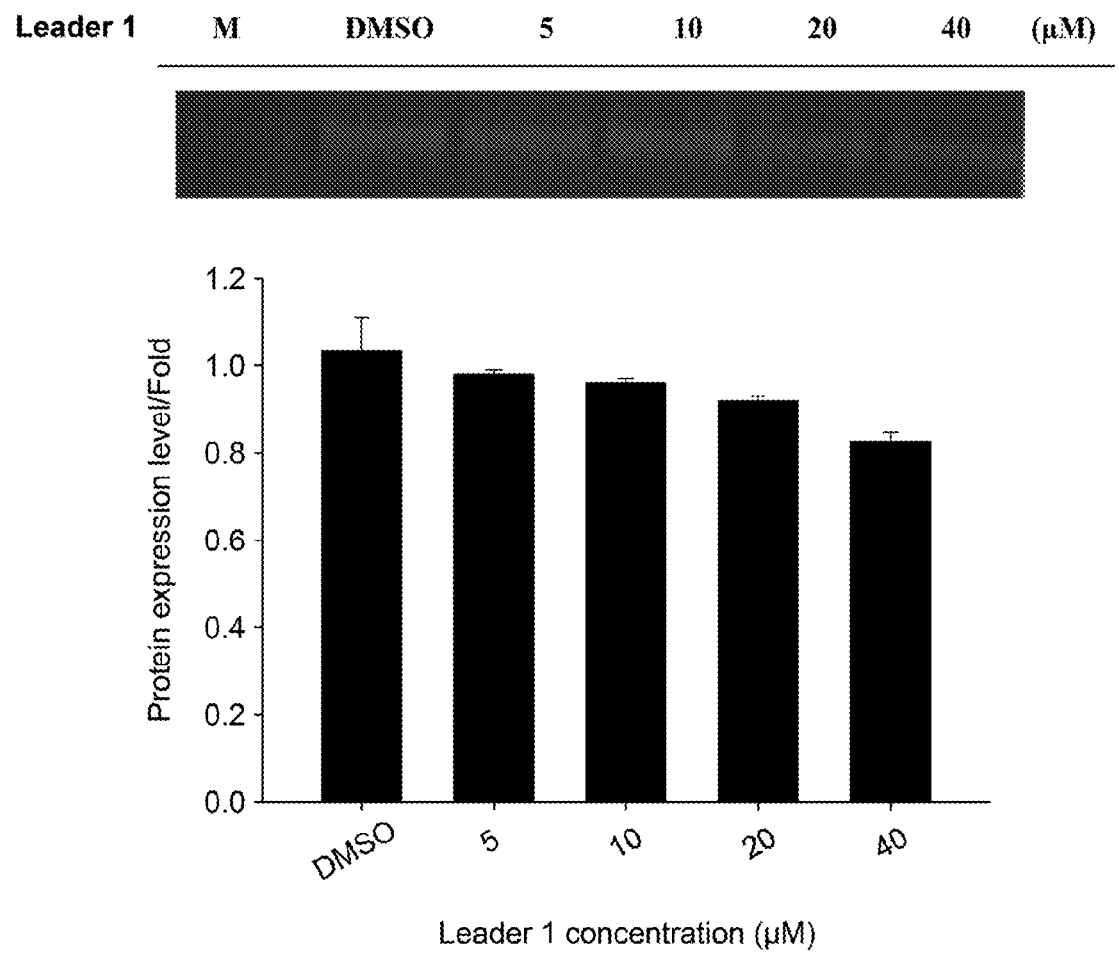
FIG. 7 is the view showing the expressions of the original plasminogen activator in lung cancer cells.

In FIG. 7, Leader 1 shows activity on suppressing plasminogen activator of lung cancer cells, especially Leader 1 having the dosage of 40 µM.

State-of-Use 10: Using Leader 1 for Obtaining Ability on Suppressing Related Proteases that Promote Metastasis of Lung Cancer Cells After total proteins of the cell are obtained, an equivalent amount of proteins are added to 8-10% gradient electrophoresis gel wells at a current of 80 V and 300 mA for 240 min for separating the total proteins. The total proteins sorted according to their sizes are blotted on a polyvinylidene difluoride (PVDF) membrane at a condition using a 100 V current for 2 hr. Then, the PVDF membrane is reacted with a blocking buffer for 1 hr. Therein, the blocking buffer contains 10% w/v skim milk powder in a TBS-T buffer, and the TBS-T buffer contains a TBS buffer having 0.1% Tween 20.

Thereafter, the PVDF membrane is immersed in an antibody solution of actin (Cell signaling Co.); an antibody solution of p-Akt or protein kinase B (1:1000, Cell signaling Co.); an antibody solution of E-cadherin (1:1000, Cell signaling Co.); an antibody solution of MMP-2,9 in matrix metalloproteinase (1:1000, Santa Cruz Co.); and an antibody solution of TIMP-1 (1:1000, Cell signaling Co.). After reactions are processed at 4° C. for 12 to 24 hr, the antibody solutions are collected to be put back in a freezer at –20° C. Then 0.1% of TBS-T buffer is used for washing three times for removing non-specific bound antibodies and antigens.

Then, the PVDF membrane is immersed in an anti-mouse secondary antibody solution having horseradish peroxidase and an anti-rabbit secondary antibody solution for reaction at a room temperature for 1~2 hr. Thereafter, the antibody solutions are collected and rinsed with 0.1% TBS-T buffer for 3 times. Then, an enhanced chemiluminescene (ECL) regent is used to detect fluorescence intensity, where β-actin protein is used as a control group of expression for statistical mapping with sigma plot 10.0.

Figure 8A:
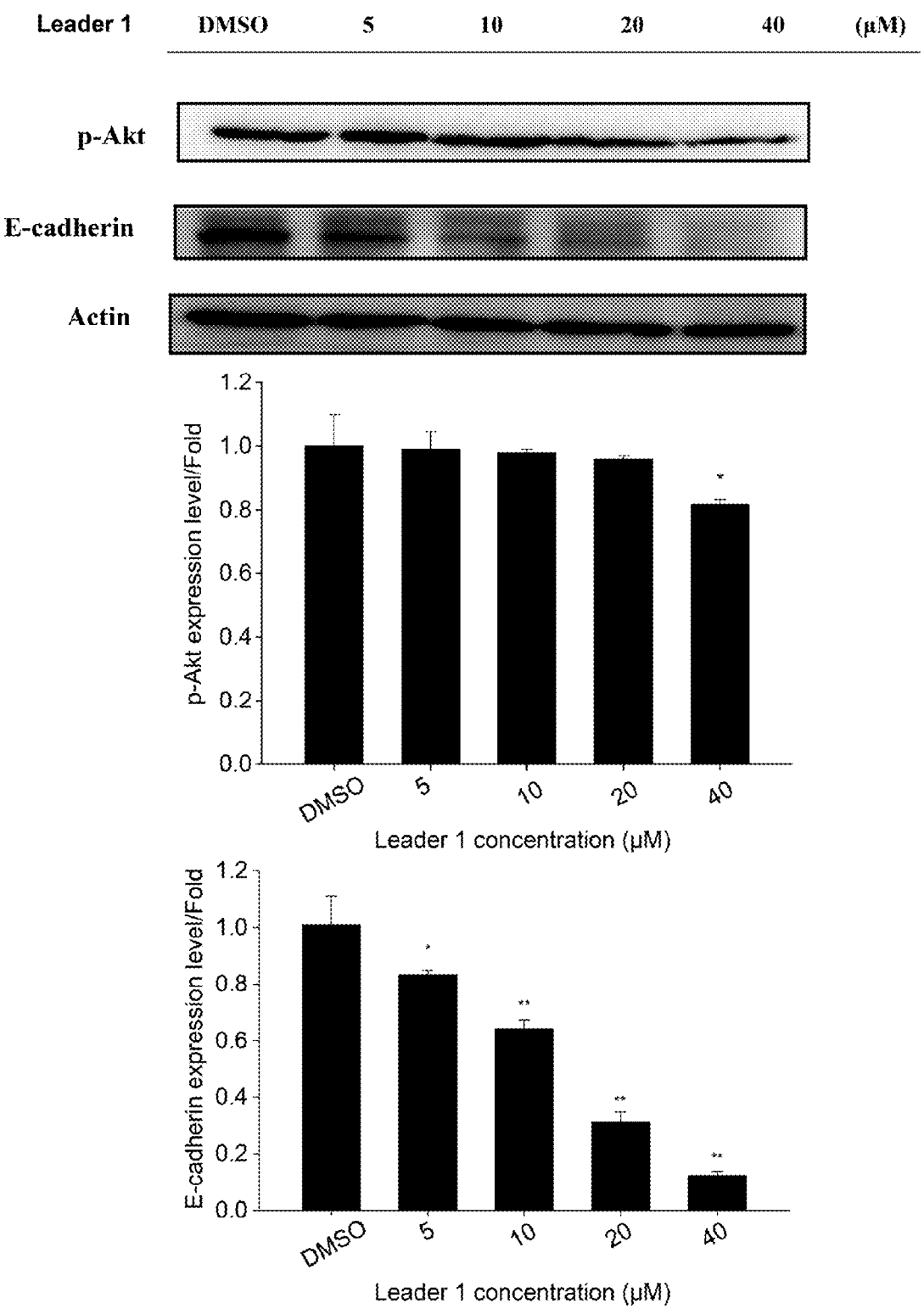
FIG. 8A and FIG. 8B are the views showing the expressions of the related proteases and proteins.
Figure 8B:
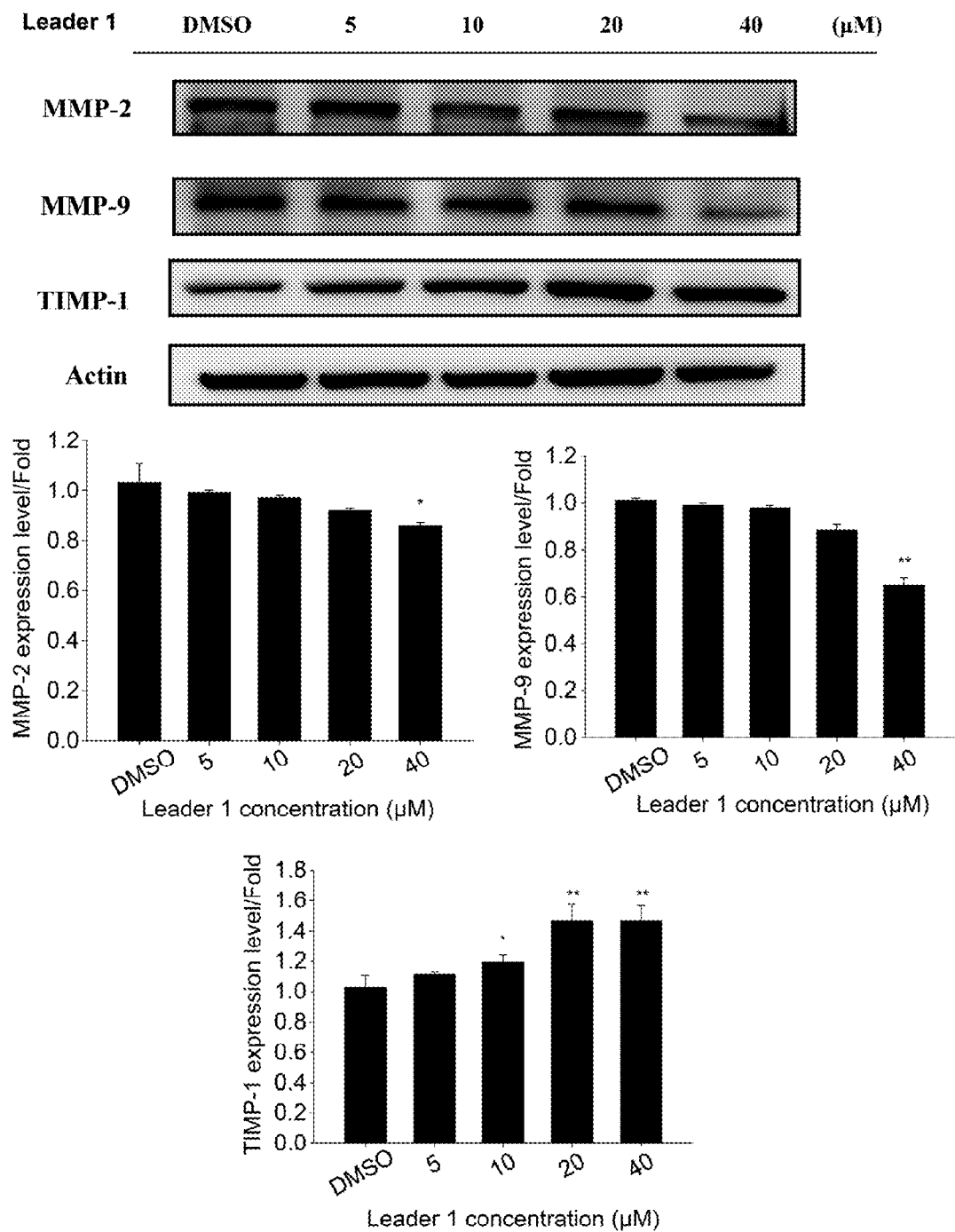

In FIG. 8A and FIG. 8B, Leader 1 shows ability on suppressing related proteases and proteins that promote metastasis of lung cancer cells.

Thus, the present invention provides a bioactive compound of A. cinnamomea mycelium, which is 2,3,6-trimethoxy-4-methylphenol and is named Leader 1. Leader 1 effectively suppresses movement, migration and invasion of lung cancer cells, and achieves the effect of anti-cancer metastasis. Leader 1 thus shows excellent resistance to physiological activity and mechanism on cancer metastasis.

To sum up, the present invention is a method of preparing a bioactive compound from solid-state cultivated A. cinnamomea mycelium for anti-metastasis against lung-cancer cells, where the bioactive compound is 2,3,6-trimethoxy-4-methylphenol and is called Leader 1; and where Leader 1 effectively suppresses movement, migration and invasion of lung cancer cells for achieving effect of anti-cancer metastasis and thus shows excellent resistance to physiological activity and mechanism on cancer metastasis.

The preferred embodiment herein disclosed is not intended to unnecessarily limit the scope of the invention. Therefore, simple modifications or variations belonging to the equivalent of the scope of the claims and the instructions disclosed herein for a patent are all within the scope of the present invention.

What is claimed is:

1. A method of preparing a bioactive compound from solid-state cultivated A. cinnamomea mycelium for anti-metastasis against lung-cancer cells, comprising steps of:
   (a1) providing A. cinnamomea mycelium, said A. cinnamomea mycelium being solid-state cultivated, said A. cinnamomea mycelium being dried; and
   (b1) extracting said A. cinnamomea mycelium by using an ethanol solution at a temperature to obtain a bioactive compound;
   wherein said bioactive compound has a formula of 2,3,6-trimethoxy-4-methylphenol having a structure as follows:

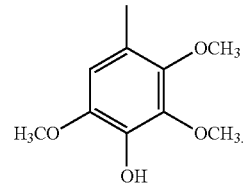

2. The method according to claim 1,
   wherein said A. cinnamomea mycelium is dried by using a cold-air dryer.
3. The method according to claim 1,
   wherein said temperature is between 25° C. and 40° C.
4. The method according to claim 1,
   wherein said ethanol solution has a concentration of volume per volume (v/v) as 95%.

* * * * *